United States Patent [19]

Tanaka et al.

[11] Patent Number: 4,820,823
[45] Date of Patent: Apr. 11, 1989

[54] PROCESS OF PRODUCING α-KETO ACIDS

[75] Inventors: Masato Tanaka, Yatabe; Toshiaki Kobayashi; Toshiyasu Sakakura, both of Sakura, all of Japan

[73] Assignee: Director-General of Agency of Industrial Science and Technology, Japan

[21] Appl. No.: 831,538

[22] Filed: Feb. 21, 1986

[30] Foreign Application Priority Data

Feb. 27, 1985 [JP] Japan .................................. 60-38297

[51] Int. Cl.[4] .............................................. C07C 51/10
[52] U.S. Cl. ..................................... 548/200; 546/327; 549/79; 549/436; 549/488; 560/254; 562/406; 562/520
[58] Field of Search ....................... 562/406, 206, 520; 548/200; 560/254; 546/327; 549/79, 436, 488

[56] References Cited

U.S. PATENT DOCUMENTS

| | | | |
|---|---|---|---|
| 4,089,431 | 8/1971 | Tanka | 562/406 |
| 4,152,352 | 5/1979 | Perron | 562/406 |
| 4,473,706 | 9/1984 | Lee et al. | 562/506 |
| 4,480,121 | 10/1984 | Klun | 562/206 |
| 4,608,816 | 5/1987 | Epstein | 562/406 |
| 4,738,802 | 4/1988 | Lee | 260/413 |

FOREIGN PATENT DOCUMENTS

WO84/02699  7/1984  PCT Int'l Appl.

OTHER PUBLICATIONS

Schoenberg et al., J. Org. Chem. 39, 3319 (1974).
Falbe, CO in Organic Synthesis, pp. 78, 118, 119 (1967).
Ozawa, Chemistry Letters (5), 567 (1985).
Tanaka, J. Mol. Catal. 32, 115 (1985).
Ozawa et al., "Double Carbonylation Reactions of . . . ", Chemistry Letters, pp. 865-868, 1982.
Fell et al, "Carbonylierung von Alkylhalogeniden . . . ", Chemiker-Zeitung, May 1985, pp. 167-170.
Fell et al., "Bildung von α-Ketocarbonsauren . . . ".
Ozawa et al., "Catalytic Double Carbonylation . . . ", Tetrahedron Letters, vol. 23, No. 33, pp. 3383-3386 (1982).
Francalanci et al., "Phase-Transfer Catalysis in Cobalt . . . ", Journal of Organometallic Chemistry, 232 (1982) 59-70.
Ozawa et al., "Palladium-Catalyzed Double Carbonylation . . . ", J. Am. Chem. Soc. 1985, 107, 3235-3245.

Primary Examiner—Robert Gerstl
Attorney, Agent, or Firm—Lorusso & Loud

[57] ABSTRACT

In accordance with a process of the present invention, α-keto acids of the general formula RCOCOOH wherein R is aryl, alkenyl or heterocyclic group, can be obtained through one-step carbonylation reaction of an organic halogenide of the general formula RX wherein R is the same as above and X is a halogen atom, with carbon monoxide and water in the presence of a basic compound and a palladium containing catalyst.

11 Claims, No Drawings

PROCESS OF PRODUCING α-KETO ACIDS

BACKGROUND OF THE INVENTION

1. Field of the Invention

This invention relates to a process of producing α-keto acids having the general formula RCOCOOH wherein R is substituted or unsubstituted aryl, alkenyl or heterocyclic group, in which an organic halogenide is carbonylated by the reaction with carbon monoxide and water in the presence of a basic compound and a palladium containing catalyst.

2. Description of the Prior Art

It is known that α-keto acids are important intermediate compounds to prepare many useful products such as α-amino acids, medicines, agricultural chemicals, polymerization initiators and other chemical products. Hitherto, such α-keto acids have been prepared by hydrolysis of acyl cyanides. For synthesis of acyl cyanide themselves, a toxic heavy metal cyanide is heat-reacted with an expensive acyl halide at an elevated temperature for a long period of time. Besides, the hydrolysis of acyl cyanide accompanies undesired side reactions through which organic acids and prussic acid are by-produced. The known processes are accordingly disadvantageous from the industrial viewpoint.

It is also known that α-keto acids are obtained by hydrolyzing hydantoin derivatives in the presence of an alkali catalyst. The hydantoin derivatives, however, are very expensive and this process is not favorable for industrial applications.

SUMMARY OF THE INVENTION

As a result of an intensive study, it has been found that α-keto acids can be produced through a double carbonylation reaction of an organic halogenide with carbon monoxide and water, which is carried out in the presence of a basic compound and a palladium containing catalyst.

It is an object of the invention to provide a novel process for the production of α-keto acids which is advantageous in industrial applications and can overcome the defects in the prior art processes.

In accordance with the present invention, there is provided a process of producing α-keto acids having the general formula RCOCOOH wherein R is selected from the group consisting of substituted or unsubstituted aryl, alkenyl and heterocyclic groups, which comprises reacting an organic halogenide of the general formula RX wherrein R has the same meaning as above and X is a halogen atom, with carbon monoxide and water in the presence of a basic compound and a palladium catalyst.

It is believed that the reaction resulting in the formation of the α-keto acid is a simple, one-step reaction expressed by the following equation (1):

$$RX + 2CO + H_2O \rightarrow RCOCOOH + HX \quad (1)$$

In the process of the invention, as understood from the above equation (1), α-keto acids can be produced through only one-step reaction in which one mole of a halogenide is reacted with 2 moles of carbon monoxide and one mole of water.

Other objects, features and advantages of the present invetion will become apparent from the detailed description of the invention to follow.

DETAILED DESCRIPTION OF THE INVENTION

In a preferred embodiment of the process of the invention, there is used an organic halogenide having the general formula RX wherein R is an organic functional group selected from the group consisting of substituted or unsubstituted aryl, alkenyl and heterocyclic groups and X is a halogen atom. Examples of suitable organic functional groups R of the organic halogenide RX are substituted or unsubstituted phenyl, tolyl, xylyl, ethoxyphenyl, phenoxyphenyl, p-biphenylyl, naphthyl, vinyl, 1- or 2-propenyl, α- or β-styryl, 2- or 3-thienyl, 2- or 3-furyl, 2- or 5-thiazolyl or the like. In case the organic functional group R is alkenyl, 1-alkenyl groups having 1 to 8 carbon atoms are preferred. The organic functional group R may optionally have one or more inert substituents except those having active hydrogen such as amino and carboxyl groups. Suitable inert substituents of the organic fuctional group R include, for example, alkoxy, aryloxy, acyl, alkoxycarbonyl, acyloxy, nitrile, hydroxyl and the like. When an organic iodide is used as a starting material RX, the organic functional group R may be substituted with other halogen atoms such as chlorine and bromine because they have much less reactivity than iodine and is therefore regarded as inert.

As a halogen atom X of the organic halogenide RX, iodine and bromine are preferred in view of reactivity to a palladium containing catalyst.

The process of the present invention is considered to proceed according to the afore-mentioned rection equation (1). In this case, the reaction rate can be effectively promoted by an basic compound, because the basic compound can take up hydrogen halogenide which is produced together with α-keto acid. Illustrative of suitable basic compounds are organic basic compounds including, for example, tertiary amines such as trimethyl amine, triethyl amine, triamyl amine, N,N-dicyclohexylmethyl amine and N-methyl pyrrolidine and derivatives thereof, or inorganic basic compounds including, for example, calcium hydroxide, calcium oxide, sodium carbonate and the like. The basic compound is generally used in an amount of at least equi-mole of the organic halogenide. Among these basic compounds, tertiary amines are preferred because they can also serve as a solvent for the reaction process when used in an excess amount.

The water which is present in the process of the invention, is generally employed in an amount of at least equi-mole, preferably 10 to 1000 moles per mole of the organic halogenide.

The process of the invention can proceed at a favorable reaction rate when it is carried out in the presence of a palladium containing catalyst. The palladium containing catalyst used in the process of the invention may be any palladium containing substance which is known, as a carbonylation catalyst, to those skilled in the art. Examples of suitable palladium containing catalysts include metallic palladium such as palladium black or palladium carbon, zero-valent, palladium complexes such as tetrakistriphenylphosphine palladium, tetrakistriphenylarsine palladium, dibenzylideneacetone palladium, carbonyltristriphenylphosphine palladium, and maleicacid anhydride-bis-triphenylphosphine palladium, divalent palladium salts or complexes such as dichlorobistriphenylphosphine palladium, dichlorobistri(p-methoxyphenyl)phosphine palladium, dichlorobistributylphosphine palladium, dichlorobisdiphenylethylphosphine palladium, dichlorobistricyclohexylphosphine palladium, dichlorobisbenzonitrile palladium, dibromobistriphenylphosphine palladium, chloropropenyl palladium, dichlorobiscyanobenzene palladium, dichloro-1,4-bis(diphenylphosphino)butane palladium, dichlorobistriphenylarsine palladium, dibromobistriphenylarsine palladium, dichloro-1,1'-bisdiphenylphosphinoferrocene palladium, dichloro-1,1'-bisdiphenylarsinoferrocene palladium, dichloro-α,ω-bisdiphenylphosphinoalkane palladium (wherein the alkane is linier or branched and has the carbon number of 1 to 10), dichloro-α,α'-diphenylphosphino-o-xylene palladium, palladium chloride, palladium oxide, palladium acetate and bisacetatobistriphenylphosphine palladium, organic or hydrogenated palladium complexes such as iodophenylbistriphenylphosphine palladium, iodo-p-tolylbistriphenylarsine palladium, chlorobenzoylbistriphenyl-phosphine palladium, chlorobenzoylbistriphenylphosphine palladium, iodomethylbistributylphosphine palladium, dimethyldiphenylphosphinoethane palladium and dihydridobistricyclohexylphosphine palladium, or the like. Any precursor of these palladium containing substances may be also employed in the process of the invention as long as they are reactive with the organic halogenide in the reaction system to produce an organopalladium halogenide.

In the process of the invention the use of a solvent is not critical. However, there can be used any usual inert solvent except those containing an amino group, a carboxyl group, etc. which release an active proton. Suitable slovents include benzene, toluene, hexane, ether such as dibutylether, tetrahydrofuran, acetone, acetonitrile, dichloromethane, chloroform, hexamethylphosphorotriamide (HMPA) and the like.

The α-keto acid thus produced in the process of the invention may be easily separated from the reaction mixture and purified in any conventional procedure; for example, after completion of the reaction, while maintaining the reaction mixture under the acidic condition, the desired product is extracted with a proper organic solvent and is then subjected to recrystallization for purification of the product.

In accordance with the process of the invetion, as a starting material, there is used a halogenide which is more easily available than the raw materials used in the prior art processes. Moreover, the product can be obtained by a simple one-step carbonylation reaction.

In the following examples, the process of the invetion is more fully described, but these examples are not intended to limit a scope and a nature of the invention.

EXAMPLE 1

A 50 ml autoclave was charged with 4 millimoles of iodobenzene, 5 ml of triethylamine, 1 ml of water and 0.038 millimoles of dichlorobistriphenylphosphine palladium ($PdCl_2(PPh_3)_2$). Carbon monoxide was then introduced under pressure into the autoclave until the partial pressure reached 150 atmospheres when measured at room temperature. The contents of the autoclave was reacted at a temperature of 40° C. for 72 hours. Then, the product was extracted with ether from the reaction mixture maintained under an acidic condition by the addition of chloric acid. As a consequence, pure benzoylformic acid was obtained in a yield of 30%.

EXAMPLES 2 THROUGH 6

In Examples 2 to 6, the same prodedure as in Example 1 was repeated except that the reactants and the reaction conditions employed in the process were varied as shown in Table I. The results of the examples are also shown in Table I wherein the yield of each α-keto-acid is determined by means of a gas-liquid partition chromatography (GLC) on the basis of the coressponding methylester obtained by reacting α-keto-acid with diazomethane which is generated by treating N-nitrosomethylurea with potassium hydroxide.

TABLE I

| Example No. | Organic Halogenide (%) (RX) | CO Pressure (atm.) | Reaction Temp. (°C.) | Reaction Time (hr.) | Yield (%) (RCOCOOH) |
| --- | --- | --- | --- | --- | --- |
| 2 | $C_6H_5I$ | 150 | 60 | 36 | 40.3 |
| 3 | $C_6H_5I$ | 150 | 40 | 70 | 37.2 |
| 4 | p-$CH_3C_6H_4I$ | 150 | 60 | 48 | 35.0 |
| 5 | (methylenedioxyphenyl iodide) | 150 | 60 | 72 | 42.0 |
| 6 | 2-iodothiophene | 150 | 80 | 10 | 47.1 |

EXAMPLES 7 THROUGH 14

A 50 ml autoclave was charged with 2 millimoles of iodobenzene, 4 millimoles of triethylamine, 0.02 millimoles of $PdCl_2(PPh_3)_2$ and one mole of water. Into the autoclave were further added various inert solvents recited in Table II. The contents of the autoclave were reacted at a temperature of 80° C. under a carbon monoxide pressure of 150 atmospheres for 90 minutes. The results of the examples are shown in Table II with respect to a conversion rate of iodobenzene and a selectivity to the α-keto acid in carbonylated products.

TABLE II

| Example No. | Solvent used | Conversion Rate of iodobenzene (%) | Selectivety to α-keto acid (%) |
| --- | --- | --- | --- |
| 7 | $CH_3CN$ | 97.2 | 41.3 |
| 8 | THF | 90.1 | 42.1 |
| 9 | Benzene | 44.2 | 58.2 |
| 10 | Methylene Chloride | 88.5 | 75.7 |
| 11 | Acetone | 94.4 | 36.7 |
| 12 | Ether | 17.7 | 43.9 |
| 13 | Chloroform | 83.6 | 74.2 |
| 14 | N,N'—Dimethyl-imidazolizinone | 93.6 | 74.2 |

EXAMPLES 15 THROUGH 25

The procedure of Example 11 was repeated except that a variety of palladium containing catalysts were employed instead of PdCl$_2$(PPh$_3$)$_2$ (Examples 15 to 23 and Example 25) and that the additives were further added to the reaction mixture (Examples 20, 21 and 24). The results are shown in Table III.

TABLE III

| Example No. | Palladium catalyst | Additive (millimol) | Selectivity to RCOCOOH (%) |
|---|---|---|---|
| 15 | PdCl$_2$[P(p-CH$_3$OC$_6$H$_4$)$_3$]$_2$ | | 71.2 |
| 16 | PdCl$_2$[P(C$_4$H$_9$)$_3$]$_2$ | | 52.2 |
| 17 | PdCl$_2$[P Ph*$_2$(C$_2$H$_5$)]$_2$ | | 59.8 |
| 18 | PdCl$_2$[P(cyclo-C$_6$H$_{11}$)$_3$]$_2$ | | 79.0 |
| 19 | PdBr$_2$(P Ph$_3$)$_2$ | | 76.1 |
| 20 | ($\pi$-C$_3$H$_5$)PdCl | P(OPh)$_3$(0.06) | 66.6 |
| 21 | PdCl$_2$(Ph CN)$_2$ | PPh$_2$(OC$_2$H$_5$)(0.08) | 71.3 |
| 22 | PdCl$_2$(dppb**) | | 39.9 |
| 23 | PdCl$_2$(AsPh$_3$)$_2$ | | 48.7 |
| 24 | PdCl$_2$(P Ph$_3$)$_2$ | P Ph$_3$(0.04) | 83.0 |
| 25 | Pd O | | 33.0 |

*Ph = Phenyl
**dppb = 1,4-bis(diphenylphosphino)butane

EXAMPLES 26 THROUGH 28

The procedure of Example 11 was repeated except that the basic compounds shown in Table IV were employed instead of triethylamine. The results are shown in Table IV.

TABLE IV

| Example No. | Base | Selectivety to RCOCOOH (%) |
|---|---|---|
| 26 | CH$_3$N(cyclo-C$_6$H$_{11}$)$_2$ | 85.0 |
| 27 | N(n-C$_3$H$_7$)$_3$ | 78.4 |
| 28 | CH$_3$N(i-C$_3$H$_7$)$_2$ | 83.3 |

EXAMPLE 29

The procedure of Example 10 was repeated except that sodium carbonate was employed instead of triethylamine and the reaction time was 6 hours. After methylesterification of the reaction product, it was subjected to a quantitative analysis by gas-liquid partition chromatography (GLC), which showed that methyl benzoylformate was obtained in a yield of 8.3% with respect to iodobenzene.

EXAMPLE 30

The procedure of Example 29 was repeated except that calcium hydroxide was employed instead of sodium carbonate. The analysis by GLC showed that methyl benzoylformate was obtained in a yield of 9%.

EXAMPLES 31 THROUGH 38

In each of the examples, the procedure of Exsample 10 was repeated except that a variety of halogenides are recited in Table V were employed instead of iodobenzene and the reaction temperature and time were varied appropriately. The results are shown in Table V.

TABLE V

| Example No. | Organic Halogenide (%) (RX) | Reaction Temp. (°C.) | Reaction Time (hr.) | Selectivity to RCOCOOH (%) |
|---|---|---|---|---|
| 31 | 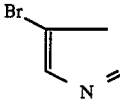 | 80 | 3 | 36.0 |
| 32 | 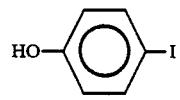 | 60 | 3 | 42.0 |
| 33 | 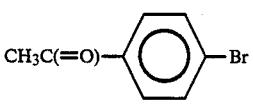 | 80 | 20 | 19.0 |
| 34 | C$_6$H$_5$CH=CHI | 40 | 10 | 6.0 |
| 35 | 2-bromothiophene | 80 | 10 | 46.0 |
| 36 | 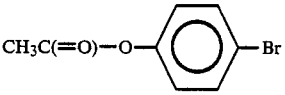 | 100 | 20 | 10.0 |

TABLE V-continued

| Example No. | Organic Halogenide (%) (RX) | Reaction Temp. (°C.) | Reaction Time (hr.) | Selectivity to RCOCOOH (%) |
|---|---|---|---|---|
| 37 | 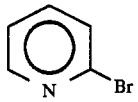 | 80 | 20 | 40.0 |
| 38 | C<sub>6</sub>H<sub>5</sub>Br | 120 | 60 | 32.0 |

In the foregoings, the invention has been shown and described with reference to preferred embodiments thereof, but it will be understood by those skilled in the art that various modification and changes can be made therein without departing from the spirit and scope of the invention.

What is claimed is:

1. A process of producing an α-keto acid having the general formula

RCOCOOH wherein R is selected from the group consisting of substituted or unsubstituted aryl, alkenyl and heterocyclic groups, which comprises reacting an organic halogenide having the general formula RX wherein R has the same meaning as above and X is a halogen atom, with carbon monoxide at a partial pressure of at least 10 atmospheres and water in the presence of basic compound and a palladium containing catalyst, in accordance with the equation:

RX+CO+H$_2$O→RCOCOOH+HX.

2. A process according to claim 1, wherein R is selected from the group consisting of substituted or unsubstituted phenyl, naphthyl, 1-alkenyl having 1 to 8 carbon atoms, α- or β-styryl, 2- or 3-thienyl, 2- or 3-furyl and 2- or 5-thiazolyl.

3. A process according to claim 1, wherein X is iodine or bromine.

4. A process according to claim 1, wherein said basic compound is a tertiary amine.

5. A process according to calim 1, wherein said palladium containing catalyst is dichloro-bistriphenylphosphine-palladium, dichloro-bistri(p-methoxyphenyl)-phosphine-palladium, dichloro-bistributylphosphine-palladium, dichloro-bisdiphenylethylphosphine-palladium, dichloro-bistriphenylphosphine-palladium, dibromo-bistriphenylphosphine-palladium, chloropropenyl palladium, dichloro-biscyanobenzene-palladium, dichloro-1,4-bis(diphenylphosphino)butane-palladium, dichloro-bistriphenylarsine-palladium or palladium oxide.

6. A process according to claim 1, wherein said water is used in an amount of 1 to 1000 moles per mole of the organic halogenide.

7. A process according to claim 1, wherein said palladium containing catalyst is used in an amount of 0.00001 to 0.1 mole per mole of the organic halogenide.

8. A process according to claim 1, wherein the reaction is carried out at a temperature of 0° C. to 200° C.

9. A process according to claim 1, wherein the reaction is carried out at a temperature of 10° C. to 150° C.

10. A process according to claim 1, wherein the reaction is carried out in the presence of an inert organic solvent.

11. A process according to claim 1, wherein said inert organic solvent is benzene, toluene, hexane, ether, tetrahydrofuran, hexamethylphosphorotriamide, acetone, acetonitrile, dichloromethane or chloroform.

* * * * *

UNITED STATES PATENT AND TRADEMARK OFFICE
CERTIFICATE OF CORRECTION

PATENT NO. : 4,820,823
DATED : April 11, 1989
INVENTOR(S) : TANAKA et al

It is certified that error appears in the above-identified patent and that said Letters Patent is hereby corrected as shown below:

Col. 1, line 24, after "cyanide" insert --usually--;

line 51, "wherrein" should read --wherein--; and line 67, "invetion" should read --invention--.

Col. 2, line 11, "ethoxy" should read --methoxy--;

line 31, "rection" should read --reaction--;

line 33, "an basic" should read --a basic--; and line 60, delete the comma "," after "zero-valent".

Col. 3, line 11, "linier" should read --linear--;

line 49, "slovents" should --solvents--; and line 61 and 66, "invetion" should read --invention--.

Col. 4, line 10, "was" should read --were--;

line 17, "prodedure" should read --procedure--; and

UNITED STATES PATENT AND TRADEMARK OFFICE
CERTIFICATE OF CORRECTION

PATENT NO. : 4,820,823

DATED : April 11, 1989

INVENTOR(S) : TANAKA et al

It is certified that error appears in the above-identified patent and that said Letters Patent is hereby corrected as shown below:

line 23, "coressponding" should read --corresponding--.

Col. 5, Table IV, "Selectivety" should read --selectivity--.

Col. 6, line 36, "Exsample" should read --Example--; and line 37, "are" should read --as--.

Claim 5, line 1, "calim" should read --claim--.

Signed and Sealed this

Seventh Day of August, 1990

*Attest:*

HARRY F. MANBECK, JR.

*Attesting Officer*     *Commissioner of Patents and Trademarks*